(12) United States Patent
Treadway Fancher

(10) Patent No.: US 7,290,290 B2
(45) Date of Patent: Nov. 6, 2007

(54) DISPOSABLE, CONTAMINANT/WATER RESISTANT, ELASTICIZED PROTECTIVE LIMB AND BODY COVERS

(75) Inventor: Rebecca Ann Treadway Fancher, 907 Warren Dr., W. Monroe, LA (US) 71291

(73) Assignee: Rebecca Ann Treadway Fancher, West Monroe, LA (US)

( * ) Notice: Subject to any disclaimer, the term of this patent is extended or adjusted under 35 U.S.C. 154(b) by 150 days.

(21) Appl. No.: 10/747,540

(22) Filed: Dec. 29, 2003

(65) Prior Publication Data

US 2004/0199974 A1    Oct. 14, 2004

Related U.S. Application Data

(63) Continuation-in-part of application No. 10/331,547, filed on Dec. 31, 2002, now abandoned.

(51) Int. Cl.
 *A41D 13/08* (2006.01)
(52) U.S. Cl. ............................................................ 2/16
(58) Field of Classification Search ...................... 2/59, 2/16, 20; 128/877–879, 846; 602/3, 5, 20, 602/23
 See application file for complete search history.

(56) References Cited

U.S. PATENT DOCUMENTS

| | | | |
|---|---|---|---|
| 2,244,871 A * | 6/1941 | Guinzburg ........................ 2/59 |
| 4,036,220 A | 7/1977 | Bellasalma ................... 128/82 |
| 4,646,727 A * | 3/1987 | Chambers ....................... 602/3 |
| 4,911,151 A | 3/1990 | Rankin et al. ................ 128/82 |
| 5,063,919 A | 11/1991 | Silverberg | |
| 5,083,557 A | 1/1992 | Lennon | |
| 5,592,953 A * | 1/1997 | Delao ......................... 128/882 |
| 5,643,183 A | 7/1997 | Hill | |
| 5,720,713 A * | 2/1998 | Hutchison ....................... 602/3 |
| 6,126,621 A * | 10/2000 | Aceves ........................... 602/3 |
| 7,020,899 B1 | 4/2006 | Carlopio | |
| 2003/0191419 A1* | 10/2003 | Melin et al. ................... 602/3 |
| 2003/0191424 A1* | 10/2003 | Skinner ....................... 602/62 |

* cited by examiner

*Primary Examiner*—Katherine Moran

(57) ABSTRACT

A disposable, yet re-usable, clear plastic protective covering, preferably clear, but not limited in color or clarity, designed to enclose articles or areas of the body in an air tight, thus waterproof environment and fitted to the body by means of simple single or multiple bands of elastic, permanently attached to the open end(s) by heat sealing, sewing or gluing with an adhesive, around the circumference of the device opening, to secure the device in place for the duration of use providing single-handed application and removal, and preventing exposure to damaging moisture, fluids or other contaminants to the area of concern for use in medical or non-medical situations.

6 Claims, 5 Drawing Sheets

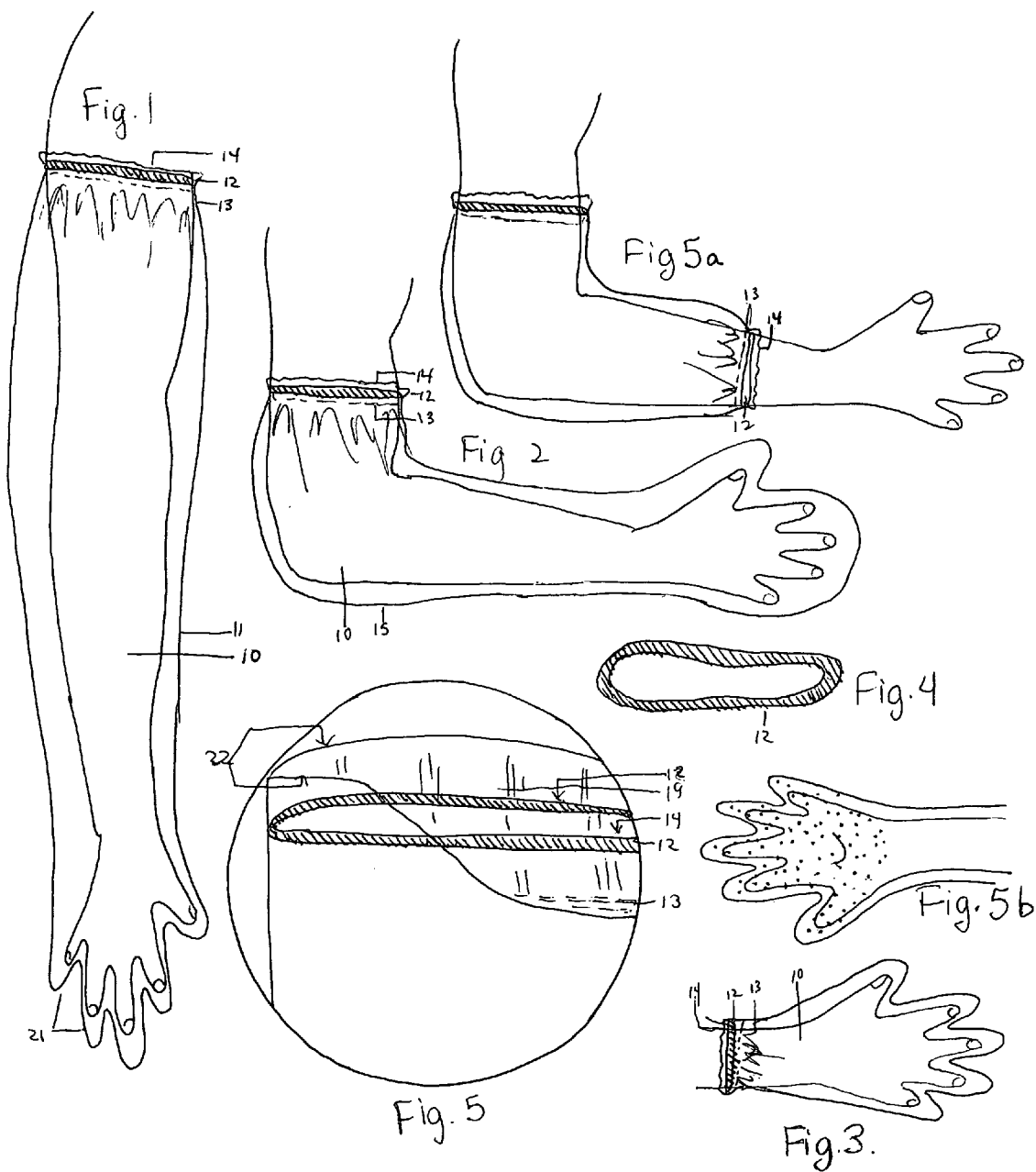

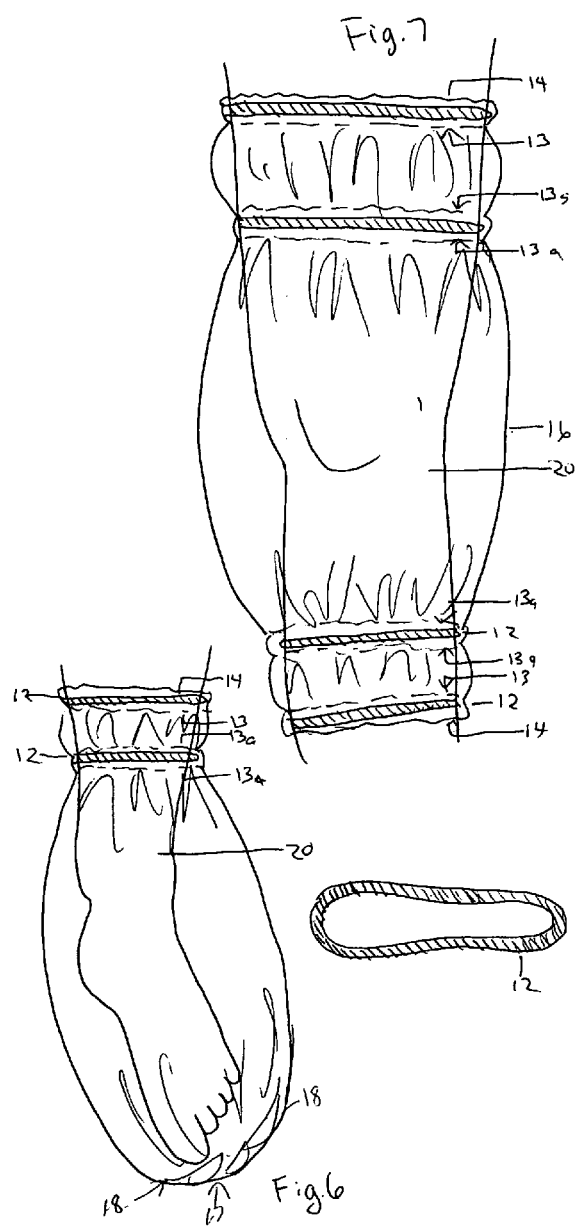
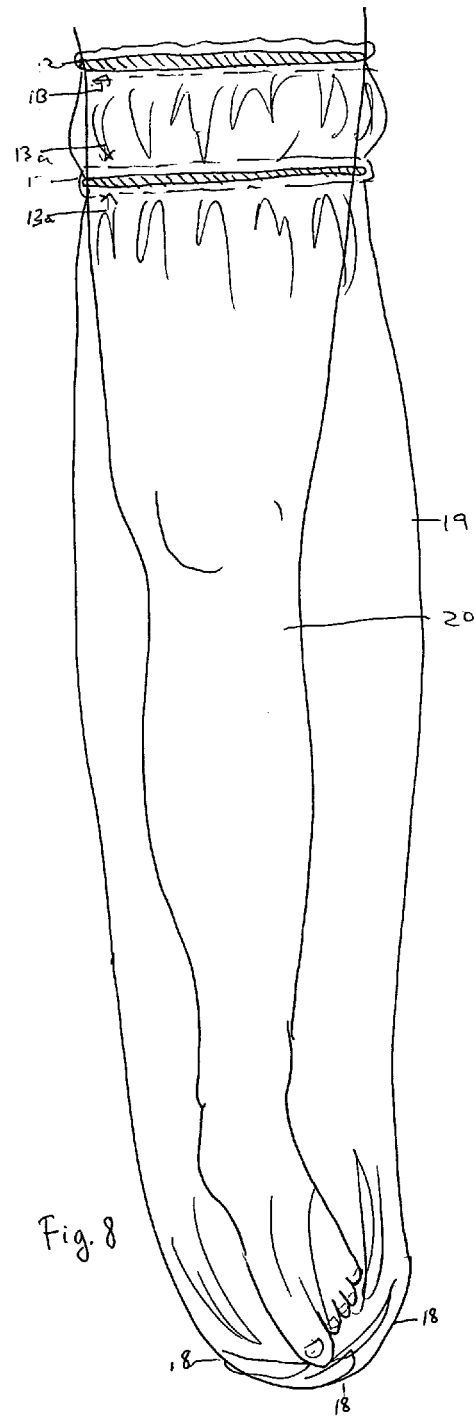

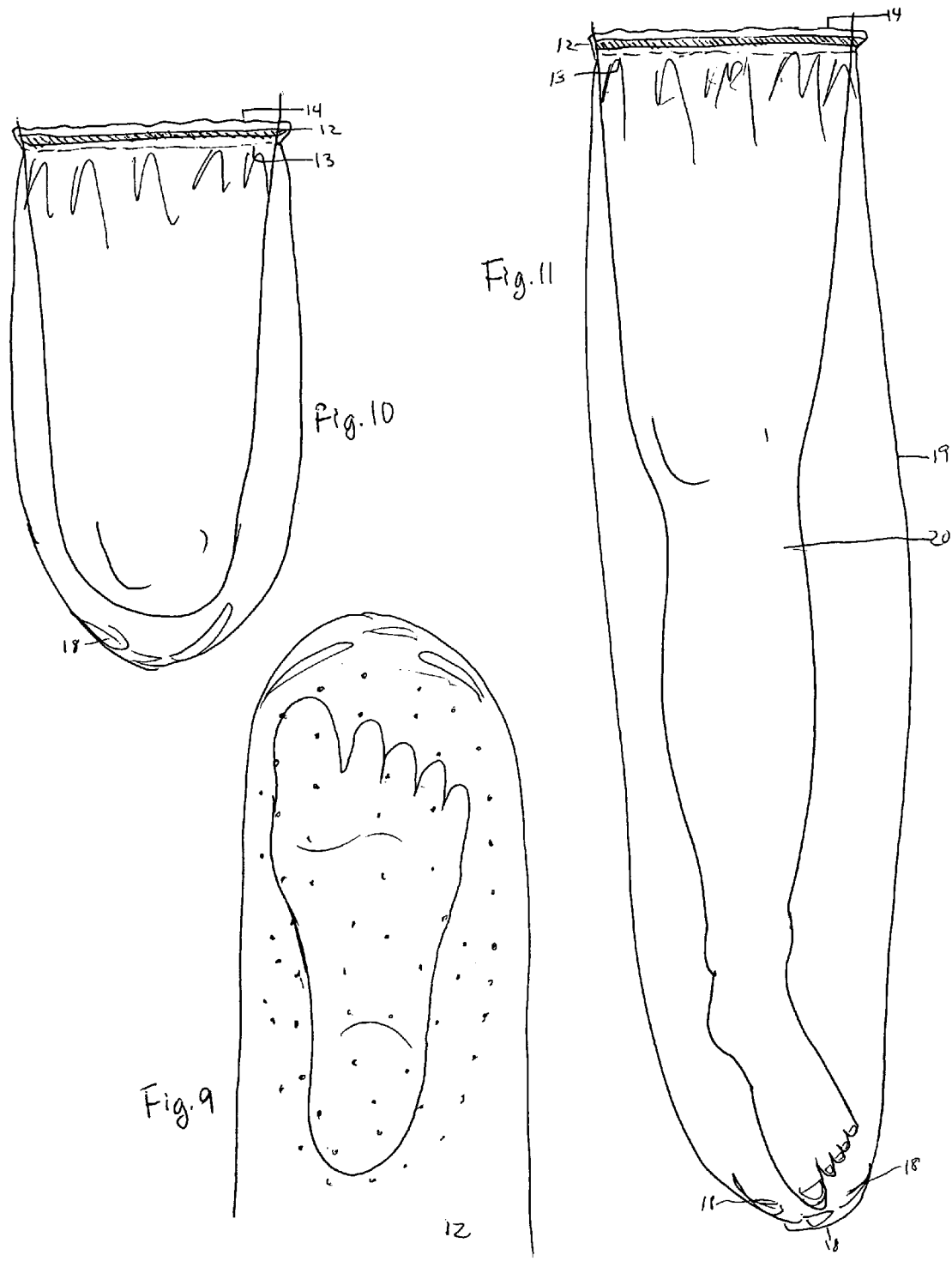

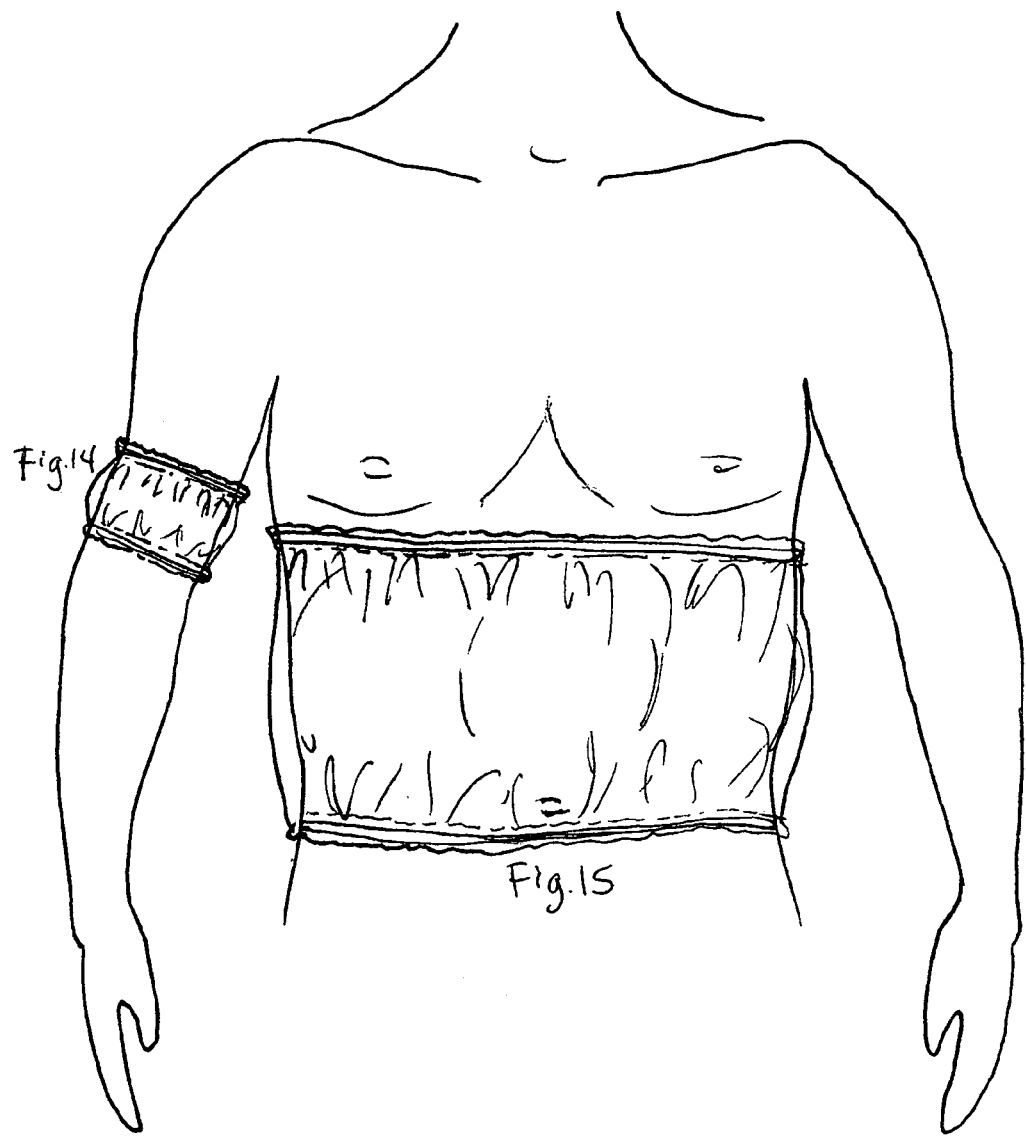

DISPOSABLE, CONTAMINANT/WATER RESISTANT, ELASTICIZED PROTECTIVE LIMB AND BODY COVERS

CROSS REFERENCES TO RELATED APPLICATIONS

This is a continuation in part of application Ser. No. 10/331,547 filed Dec. 31, 2002, now abandoned

| | | | |
|---|---|---|---|
| 4,911,151 | March 1990 | Rankin et. al. | 128/82 |
| 5,063,919 | November 1991 | Silverberg | |
| 5,643,183 | June 1995 | Hill | |
| 4,036,220 | October 1975 | Bellasalma | 128/82 |
| 5,083,557 | August 1990 | Lennon | |

STATEMENT REGARDING FEDERALLY SPONSORED RESEARCH AND DEVELOPMENT

REFERENCE TO A "MICROFICHE APPENDIX"

BACKGROUND OF THE INVENTION (1) Field of the Invention

The invention of these devices relates to the protection of various body parts from damaging moisture or other contaminants, during bathing procedures, normal daily activities, or other uses when the wearer wishes an area to be kept clean, dry or protected, usually involving an injury covered by, but not limited to casts, dressings or the use of sutures, surgical staples, rashes, wounds, amputations, vaccines, IVs, tattoos, etc. The clear plastic, disposable, but re-usable devices, elasticized at the openings, are simply designed for single-handed application and contain no additionally attached or unattached straps, ties or closures. These devices are not limited to medical uses for personal injuries or situations, but may be used by individuals for personal protection to prevent a non-injured area of concern from being exposed to harmful fluids or other contaminants, including, but not limited to body fluids, such as in emergency situations involving injured individuals, animals, etc.

(2) Description of Related Art

While there are other waterproof coverings for casts or wound dressings primarily intended for bathing purposes, such as is indicated in U.S. Pat. No. 5,063,919 Silverberg, U.S. Pat. No. 5,643,183 Hill and U.S. Pat. No. 4,911,151 Rankin et. al., this invention can be used effectively not only for that purpose, but also as a barrier for wound or skin protection from other contaminants or air-borne pollutants, and not limited to medical situations.

A typical form of water-resistant protection for a cast or dressing is the use of a garbage bag or plastic grocery bag, tied, rubber-banded or taped at the opening in an attempt to create a waterproof covering. Even in hospitals, wound dressings are often occluded with stretchable plastic wrap, normally used as a food container covering. Again, tape is often used to seal the edges in an attempt to make the area airtight or waterproof. Frequently, these methods are ineffective at best and potentially harmful to the wearer at worst and render the item useless after a single use. Not only are these items not manufactured to be waterproof coverings for injuries, which often leak between layers or gathers near the openings, but also the wearer could suffer skin abrasions or allergies from the adhesive used to close the opening around the area of concern, compounding the original problem.

These methods are ineffective as well as time-consuming, and must require at least two hands for application, often needing the help of a second party.

Available or patented cast protectors are generally made from a heavy plastic or vinyl sheeting, such as U.S. Pat. No. 5,643,183 Hill, and U.S. Pat. No. 5,063,919 Silverberg, and are meant for re-use for the duration of convalescence of the wearer, thus making the product quite costly.

This invention is made from polyethylene sheeting with thickness of approximately, but not limited to, 1.5 mil, providing durability, strength and stretchability as well as affordability. While these items may be re-used, even for the duration of the injury, they are intended to be disposable, encouraging the wearer to replace the item several times during the length of needed use. This is preferable to the same item being used over and over indefinitely, thus running both the risk of damage, which could lead to the wearer attempting to repair a damaged item and promoting possible leakage and damage to the cast or dressing, possibly causing a setback in recovery, as well as the probability that an item used in water so frequently will begin to harbor mildew and bacteria, which could be injurious to the wearer.

Prior art contains various and even complicated means of closure for the open end of the protective device. U.S. Pat. No. 4,036,220 Bellasalma mentions a "foam-like cushioned band secured to the member with adhesive and a flexible collar mounted to the cushioned band which will overlap and be secured by a combination of hooks and loops (Velcro). A similar closure is used in U.S. Pat. No. 5,643,183, Hill. Such closures can result in the gathering of excess sleeve material, creating a waterpath, as suggested in U.S. Pat. No. 4,911,151 Rankin et. al. Furthermore, the use of such a closure prohibits flexibility with the movement of the limb, which would result either in significant leakage or the inconvenient re-adjustment during use.

Elastic is also used as a common closure for protective wear. Often, it is used as a strip, wrapped around the limb, similar to the use of a tourniquet as is described in U.S. Pat. No. 4,911,151, Hill. Another example of a tourniquet effect is seen in U.S. Pat. No. 5,063,919 Silverberg. Rather than using a more than 360' wrap, as disclosed in the Hill description, elastic straps are positioned in several parallel bands covered with plastic strips, except for an area in the front and the back of the protective covering. In that particular patented design, these open areas are to be adjusted with a 'dumbbell' type object to be inserted in the loops in the ends of the elastic bands, and twisted around several times until it cannot be twisted further. Both of these methods of using elastic could be extremely harmful to the wearer if overtightened or left on too long, particularly by those wearers with diseases, such as diabetes, who have circulatory problems.

A flange is used in G.K. Guinzburg's U.S. Pat. No. 2,244,871 for a waterproof protective device. The flange described by Guinzburg indicates the piece is either cut from a flat rubber or latex material, which is no longer considered an acceptable material for medical concerns, and 'vulcanized' to the body of the protective device, or integrated into the device by molded design. Guinzburg states that the inner circumference or 'length' of the flange is less than the length of the edge, presuming this pertains to circumference, and indicating this piece is of a certain width to accommodate the difference in circumference. Guinzburg also indicates tat the flange is located a distance from the edge or opening of his device which would permit pooling at the opening. He also states that more than one flange can be present, allowing up to three flanges to be incorporated into the design if necessary. According to Frank Vincent Carlopio, U.S. Pat. No. 7,020,899, "this kind of sealing mechanism is vulnerable to loosening with perspiration from exercise, is vulnerable to pressure from an external fluid, and concentrates the sealing force on a relatively narrow area, which would have a tendency to restrict the blood flow." Guinzburg also states that the 'flange fits in downwardly extending position' which would encourage pooling water to enter the area to be protected.

In U.S. Pat. No. 4,646,727, David H. Chambers cites using elastic encased at the opening of his east protector. The elastic is encased in the fabric of Chambers'invention by method of sewing. However, the invention described by Chambers is not used for bathing purposes or medical purposes and is not made from water resistant polymeric material, for which sewing would not be a method of choice. Therefore, Chambers'invention is not meant to protect an area of concern from moisture damage.

Additionally, each prior example requires the excess edge of the sleeve covering to rise above the elastic, forming a lip or cupped edge which would collect water during the process of bathing, and lead to considerable seepage during removal of the protector.

Concerning prior art of similar type foot designs, U.S. Pat. No. 5,083,557 Lennon, shows a podiatry boot made in the shape of a boot with an adhesive closure at the open edge. While it is made of similar type disposable materials as the present invention, the boot shape itself would limit the size of the foot to be covered. The opening would then be wrapped around the leg above the ankle, folding in the excess, and the ends of the folded areas would be secured with adhesive.

Adhesive is also used in U.S. Pat. No. 4,911,151 Rankin, et. al. as it is attached to an elastic strap to be wound around the opening of the protector and adhered or 'stuck' into position. In both cases, if the position is not accurate the first time, the adhesive either would damage the protector during its removal and readjustment or it would lose its ability to stick effectively on a second attempt, rendering it useless for its intended purpose, or after only a single use. Furthermore, should the adhesive contact water or other contaminant prior to bonding with the receiving material, the seal would not take hold in the initial attempt and could never be used as intended.

The current invention (my invention) involves the use of circular elastic bands at the open edges. The strength and stretch-ability of the bands provide a snug, but comfortable fit for the wearer, preventing water seepage. Located at the open edge of the device, each piece contains either a single band, mostly for arm or long term wear items, or double bands placed parallel and separated by a space, mostly for the leg items. These bands are attached in such manner that allows the elastic to be positioned in the interior of the finished device. Placed in this manner, these bands allow both single-handed application for the wearer and the flexibility to conform to the movement of the limb. There is no need for adjustment, since the band relies on its 'memory' ability to stretch and return, and there is no need for concern of over-tightening. Additionally, the placement of the elastic prevents water seepage and the double band design allows for added protection if needed, allowing the casing of the inner band to serve as a ledge or 'catcher' for seepage.

The size of the opening of the present invention is reasonably larger than an average limb size, but not excessive, such as with a garbage bag, which eliminates the possibility of deep gathers caused by the elastic, thus eliminating the chance of leakage. The elastic is of a content known for its memory, therefore stretching beyond the circumference of the opening, but returning to its original size, which allows the item to be re-used.

The simple design of these items would allow similar items to be made in like manner for other parts of the body, such as the torso.

BRIEF SUMMARY OF THE INVENTION

The purpose of the present invention is to eliminate the problems of the prior inventions and create a disposable, yet re-usable and affordable design that will offer protection for the wearer from harmful or damaging fluids, moisture or other contaminants. This invention would primarily be used for the protection of casts, IVs, surgery sites, burns, rashes, dressings, wounds, amputations, vaccines, tattoos, etc, but not limited to medical uses.

This invention will provide a simple, yet effective covering designed for comfort and single-handed application to allow the wearer adequate coverage for normal daily routines, such as bathing, and more independence to perform these activities, making recovery time simpler and easier.

This present invention includes the use of a water-resistant plastic material, such as polyethylene film, preferably clear, but not limited to color or clarity, and formed into a protective cover for the limbs or other body areas and gathered at the openings with elastic band sealed to the edges, and in some items, with a second band sealed into a cuff in the interior of the device, a distance parallel to the band on the end. Problems with prior art could feasibly occur because elastic positioned any distance from the edge will cause water to pool in the excess material above the elastic which will drain directly onto the injury upon removal.

The design of this invention will avoid circulatory problems of over-tightening and the problems of single-use adhesives, ties, straps, Velcro closures or other complicated devices needed to secure a reasonably leak-proof opening, all of which are present in prior inventions.

The simplicity of this present design supports the ability to be affordably disposable, although re-usable, which will promote an environment free of harmful mildew or bacteria for the injured site and the option to discard and replace as needed, should the protector become damaged or contaminated. The prolonged use of a waterproof item can often lead to such problems, even with the most attentive care, which can delay the healing process, or create further health-related issues.

In this day of prevention realistically being the 'next best cure,' a full-coverage disposable item simply makes good sense.

The palm portion of the hand designs and the underside portion of the foot designs may have gripping mechanisms such as vinyl micro-dots, known as 'power-dots' for added convenience or safety purposes. Designs may or may not have the addition of these grippers.

BRIEF DESCRIPTION OF THE SEVERAL VIEWS OF THE DRAWINGS

FIG. 1 shows an example of a full length arm, (no. 10) product, including the fingered extensions, (no. 21). Variations of this design may occur, such as a mitten or rounded off design. No. 12 represents the elastic band that is placed a distance away from the edge which is then folded (no. 14) over along the band, and heat sealed (no. 13) to the main body of the device.

FIG. 2 is a variation of FIG. 1, showing the mitten design.

FIG. 3 is a variation of FIG. 1, showing the different lengths in the arm product. Another median length can be made as well. These various lengths can be made with either variation of the arm product designs.

FIG. 4 is the continuious elastic band.

FIG. 5 shows a close-up view of the elasticized portion, pictured flat. The elastic band (no. 12) is shown going around the circumference of the opening. The open edge of the device (no. 22) is shown as it is folded (no. 14) over the band, and then a seam is heat-sealed around the edge, bonding it with the body of the device (no. 13).

FIG. 5a is another variation of the arm product, with two open ends. Both openings are elasticized using the elastic band (no. 12), placed a distance away from the edges, and folded (no. 14) over along the band, and heat sealed (no. 13) to the main body of the device.

FIG. 5b shows the palm portion of the hand/arm devices with gripping dots, similar to, but not limited to vinyl micro-dots, also known as 'power dots.' These dots are not present in all hand/arm devices, but may be used for certain types of protective devices.

FIG. 6 shows a foot/ankle variation (no. 17) of FIG. 8, which is a full leg device (no. 19). Various lengths may be made of this same leg (no. 20) design. No. 18 indicates where the end of the device is heat sealed closed. The tubular products may be folded in a manner that will create a rounded appearance, as shown in FIG. 6 and FIG. 8.

FIG. 7 is another variation of the same device, used for knees (no. 16). Each figure shown on this page indicates a double elastic (no. 12) design, used for added protection. The elastic bands (no. 12) are used in the same manner as previously described, with the folds being indicated by no. 14 and the heat seals indicated by no. 13. No. 13(a) indicates this heat seal is pressed together, and actually located behind the elastic band (no 12), which is now positioned in the interior of the device. The method of forming this seal is explained in the following detailed description as Step 2. Single or double banding may be used in any of the hand/arm or foot/leg or body products.

FIG. 9 shows the bottom of the 'foot' portion of the foot/leg device with vinyl micro-dots. These dots are not present in all foot/leg devices, but may be used for certain types of protective devices.

FIG. 10 shows a device used for amputation wounds.

FIG. 11 is a single banded full length leg product. As previously stated, all hand/arm or foot/leg or body items may be made in a variety of lengths, may contain single or double elastic bands, and may or may not have micro-dots for gripping or anti-skid purposes.

FIG. 14 shows a smaller cuff, a variation in size of FIG. 5a.

FIG. 15 is another size variation of the same design concept, used for mid-body, or torso, coverage.

DETAILED DESCRIPTION OF THE INVENTION

Figure 12:
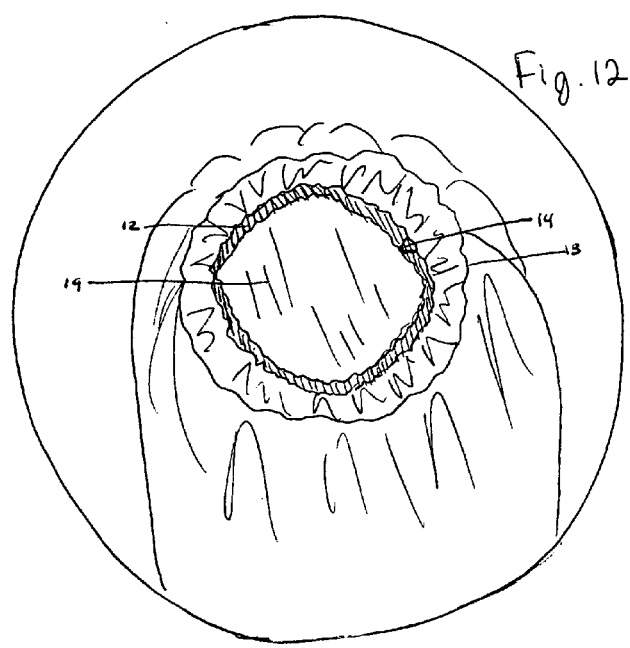
FIG. 12 shows a view from the top of a single elasticized device, into the interior which contains the part of the body to be protected.
Figure 13:
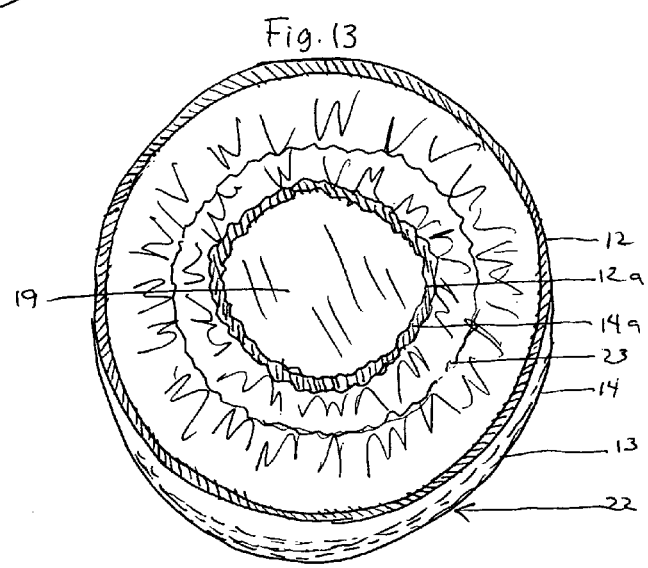
FIG. 13 shows a view from the top of a double elasticized device, into the interior (no. 19), which contains the affected body part. The band of elastic placed first is no. 12(a) in the manner described in the following detailed description as Step. 2. No. 14(a) is the folded edge which forms the ledge, or catcher, inside the device and is extremely effective in preventing any trickles of water from entering the enclosed area. Nos. 12, 13 and 14 are explained in Step. 1 of the following detailed description.

The designs of this invention are made from polyethylene film, preferably clear, but not limited in color or clarity, for continuous viewing of the covered sites or other comparable material, approximately, but not limited to 1.5 mil in thickness, doubled flat for shaped items, and tubular for the remaining designs. Standardly, the designs are shaped into air tight devices by heat-sealing the edges and/or ends, leaving an open end for the limb entrance. Some items are left open on both ends with elastic placed at both openings, such as for knees, elbows, and central body areas.

Certain arm designs, having shape for fingers, may be formed by using a heated die in the shape of the design to cut the film, sealing all touching edges together. Ref: U.S. Pat. No. 5,083,557 Lennon, beginning paragraph of "Detailed description of the invention." Variations of all designs may be implemented.

Tubular material may be used as well for certain other remaining designs, cut to the desired length and heat sealed at one open edge. Yet, other designs may be tubular in shape, but with both ends left open and elasticized in the following manner. Tubular materials or heated die cut patterns may be used for any of the designs. Each will be elasticized in the following manner, but not limited to this particular process.

Step 1) The opening of each design, either fonned by means of heated die, or cut from tubular material, is placed over a form the circumference of the opening and an elastic band is placed over the end a distance of approximately ½ to ¾ of an inch down from the edge. The edge is then folded over the elastic band until the band is in the crease of the fold, and a line seam is heat-sealed at the edge, bonding the edge of the plastic to the receiving body of the protector and enclosing the elastic band in a self-casing. The device is removed from the form, and a single elasticized opening has been made on the protector, the elastic band encased, and being drawn into the interior of the device by the strength of the band.

Designs using a double elasticized opening are fashioned in the following manner:

Step 2) The opening of the body of the protector is placed over a form the circumference of the opening. An elastic band is placed around the end of this opening and positioned a distance (ideally several inches) down from the open edge. The excess is then pulled over the elastic band until the band rests in the crease of the fold. A line seam is then sealed approximately ¾ of an inch down from the encased band, sealing the top plastic to the receiving body of the protector and enclosing the elastic band in a self-casing, and pulling this elastic inward to form the ledge or 'catcher.' The remaining inches of the edge of the plastic are then pulled up and over this elasticized casing and Step 1 is used to finish the edge. These two steps create the double elasticized opening with parallel elastic bands placed a distance approximately 2½ to 3 inches apart.

Protective devices comprising two open ends may have one elastic band encased at each end for a total of two bands, or one end may contain a double elastic closure, as described in the previous paragraph and the other end may have only one band, for a total of three bands. Furthermore, both ends may contain a double elastic closure, for a total of four bands.

Heat sealing the method of preference for encasing elastic to plastic, as is bonding or other acceptable or convenient method of attachment. This invention may not be limited to the beat sealing method described above, but may use other methods of attachment as suggested in the previous sentence.

The addition of vinyl micro-dots, or 'power dots' may or may not be present in the palm portion of the hand products, or the bottom of the foot products for gripping purposes.

What is claimed as exclusive property or privilege is:

1. A method of making a waterproof sleeve, having at least one open end, for the limbs or torso comprising the following steps:
   a. placing a tubular film material over a form sized for a human limb such that an edge of the material is exposed, positioning a first elastic band over the film material at a distance from the edge,
   b. folding the edge of the film over the band so that the band rests in a crease of the resulting fold, and sealing the folded portion, forming an encased band that is inwardly biased and forms an interior ledge to prevent liquid from entering the sleeve's interior region,
   c. positioning a second elastic band approximately 2 ½ to 3 inches below and parallel to the first band and repeating step (b), forming a second encased band that is inwardly biased and forms a second interior ledge to further prevent liquid from entering the sleeve's interior region, and whereby the encasement structure preserves the structural integrity of the bands.

2. The method of claim 1, wherein the sleeve has one open end and one closed end.

3. The method of claim 1, wherein the sleeve has two open ends, with said first and second bands provided at each end.

4. The method of claim 1, wherein the sleeve is formed from water resistant polymeric material.

5. The method of claim 2, wherein the closed end includes four finger sleeves and a thumb sleeve.

6. The method of claim 2, wherein the closed end includes a finger pocket and a thumb sleeve.

* * * * *